United States Patent [19]

Pettit et al.

[11] Patent Number: 4,996,237
[45] Date of Patent: Feb. 26, 1991

[54] COMBRETASTATIN A-4

[75] Inventors: George R. Pettit, Paradise Valley; Sheo B. Singh, Tempe, both of

[73] Assignee: Arizona Board of Regents, Tempe, Ariz.

[21] Appl. No.: 158,866

[22] Filed: Feb. 22, 1988

Related U.S. Application Data

[63] Continuation-in-part of Ser. No. 590, Jan. 6, 1987.

[51] Int. Cl.$^5$ .......................................... A61K 31/075
[52] U.S. Cl. .................................. 514/720; 514/721; 568/631; 568/646
[58] Field of Search ................ 568/631, 646; 514/720, 514/721

[56] References Cited

U.S. PATENT DOCUMENTS 4,094,994  6/1978  Schönenberger et al. ...... 514/721 X

FOREIGN PATENT DOCUMENTS 0276051  7/1988  European Pat. Off. ............ 568/646
1046380  10/1966  United Kingdom .

OTHER PUBLICATIONS

Venditti et al., *Lloydia*, 30, 332–348 (1967).
Kettenes-Van den Bosch, et al., *Chem. Abs.*, 89, 160092x (1978).
Majumder et al., *Chem. Abs.*, 102, 92950k (1985).
Crombie et al., *J. Chem. Soc. Perkin Trans. I*, "Dihydrostilbenes of Cannabis. Synthesis of Canniprene", pp. 1467–1475 (1982).
Pettit, et al., *Chem. Abs.*, 110, 4696u (1989).
Pettit, et al., *Chem. Abs.*, 109, 122076u (1988).
Pettit, et al., *Chem. Abs.*, 108, 72037p (1988).
Pettit, et al., *Chem. Abs.*, 107, 236347x (1987).
Pettit, et al., *Chem. Abs.*, 107, 112617r (1987).
Pettit, et al., *Chem. Abs.*, 103, 160277u (1985).
Pettit, et al., *Chem. Abs.*, 97, 107051x (1982).

*Primary Examiner*—John W. Rollins
*Attorney, Agent, or Firm*—Richard R. Mybeck

[57] ABSTRACT

The African tree *Combretum caffrum* (Combretaceae) has been found to contain an agent which is a powerful inhibitor of tubulin polymerization (IC50 2–3 $\mu$M), the growth of murine lymphocytic leukemia (L1210 and P388 with ED50 <0.003 mg/ml and human colon cancer cell lines (e.g. VoLo with ED50 <0.01 $\mu$g/ml). This agent is herein denominated "combretastatin A-4". The structure assigned by spectral techniques was confirmed by synthesis.

3 Claims, No Drawings

COMBRETASTATIN A-4

INTRODUCTION

Partial funding for the work reported herein was provided by the National Cancer Institute, DHHS; and the Arizona Disease Control Research Commission.

This application is in-part a continuation of our co-pending U.S. patent application Ser. No. 000590 filed Jan.6, 1987 entitled "Isolation, Structural Elucidation and Synthesis of Novel Antineoplastic Substances Denominated "Combretastatins"".

BACKGROUND OF THE INVENTION

Tropical and subtropical shrubs and trees of the Combretaceae family represent a practically unexplored reservoir of new substances with potentially useful biological properties. Illustrative is the genus Combretum with 25 species (10% of the total) known in the primitive medical practices of Africa and India for uses as diverse as treating leprosy (See: Watt, J. M. et al, "The Medicinal and Poisonous Plants of Southern and Eastern Africa", E. & S. Livingstone, Ltd., London, 1962, p. 194) (Conbretum sp. root) and cancer (*Combretum latifolium*). But only a few species principally *Combretum micranthum*(used in northern Zimbabwe for mental illness) (See: Ogan, A. U., *Planta Medica*, 1972, 21, 210; and Malcholm, S. A. et al, *Lloydia*, 1969, 32, 512.) and *C. zeyheri*(for scorpion invenomation) (See: Mwauluka, K. et al, *Biochem. Physiol. Pflanzen*, 1975, 168, 15) have received any scientific study.

The present investigation was undertaken to determine the murine P388 lymphocytic leukemia (PS system) inhibitory constituents of Combretum caffrum (Eckl. and Zeyh) Kuntze (also as *C. salicifolium* E. Mey), a potentially useful lead which came out of the U. S. National Cancer Institute's world-wide exploratory survey of plants. In South Africa this tree is known by the Zulu as Mdubu (used as a charm) and is otherwise known as bushveld willow, bushwillow ans rooiblaar. The timber is principally used on African farms as scrap wood and fuel. Interestingly, honey arising from the nectar of this tree is strongly bitter but no problems have been recorded from human consumption.

BRIEF SUMMARY OF THE INVENTION

A new antineoplastic substance has been isolated, structurally elucidated and synthesized having the formula:

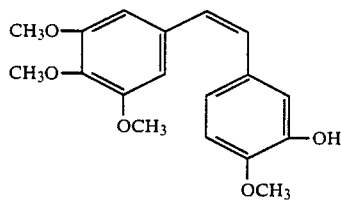

herein denominated "Combretastin A-4".

The substances are extracted from the stem wood of *Combretum caffrum* with 1:1 methylene chloride:methanol and converted to a methylene chloride fraction that was partitioned between hexane and the methanol-water (9:1) followed by adjustment to 3:2 methanol-water and extraction with methylene chloride. The methylene chloride fraction was separated by steric exclusion chromatography on Sephadex® LH-20 to obtain the fractions. The isolation of the specific substances from the fraction is detailed in the several examples reported below.

Accordingly, a principle object of the present invention is to isolate and elucidate the structure of new antineoplastic substances from *Combretum caffrum* and to provide the methodology for the efficient and reliable replication thereof by synthetic procedures.

Another object of the present invention is to provide new and useful pharmaceutical preparations containing one of the new antineoplastic substances as the essential active ingredient thereof.

These and still further objects as shall hereinafter appear are readily fulfilled by the present invention in a remarkably unexpected manner as will be readily discerned from the following detailed description of an exemplary embodiment thereof.

DESCRIPTION OF PREFERRED EMBODIMENTS

The willow-like appearance of the South African tree *Combretum caffrum* (shrub to 15 m. high, Combretaceae) is a common sight overhanging stream beds, and the powdered root bark is used by the Zulu as a charm to harm an enemy. Previously, a series of bibenzyls, stilbenes, and phenanthrenes have been isolated from this tree. All of these substances were found to possess varying degrees of activity against the murine P388 lymphocytic leukemia cell line, and some, especially those denominated combretastatins A-1 and A-2 were shown to be potent inhibitors of microtubule assembly. A trace fraction (26.4 mg from 77 kg of dry stem wood), selected due to inhibition of the P388 cell line and tubulin polymerization, has been now found to contain a powerful inhibitor of microtubule assembly (IC50 2-3$\mu$M). This agent is herein denominated "Combretastatin A-4". This cis-stilbene was found comparable in its inhibitory effects to podophyllotoxin and combretastatin A-1 and more potent than colchicine and steganacin.

The 0.65 g fraction that just preceded the one employed to separate fractions containing combretastatins A-3 and B-2 (during partition chromatography on Sephadex LH-20 in 3:1:1 hexane-toluene-methanol) was further refined by a series of liquid (3:1 and 4:1 hexane-ethyl acetate) chromatographic steps on silica gel and by HPLC (Partisil M-9, 9:1 hexane-2-propanol). While the resulting P388 active fraction (26.4 mg) at first appeared homogeneous, high field (400 MHz) $^1$H-n.m.r. suggested a mixture of at least three compounds that resisted separation until conversion (7.1 mg) to t-butyldimethylsilyl ether derivatives. Multiple development preparative layer chromatography on silica gel in 17:3 hexane-ethyl acetate afforded silyl ethers (3.0 mg, oil) and corresponding to combretastatin A-4.

To confirm results of $^1$H- and $^{13}$C-NMR and mass spectral proposals for the structure of combretastatins A-4 it was synthesized. The synthetic t-butyldimethylsilyl ether derivative was compared with the natural counterpart and found to be identical. The following synthesis of combretastatin A-4 was typical. The ylide (n-butyl lithium) from the benzyl silyl ether unit phosphonium bromide (11.9 g ) in tetrahydrofuran was treated (10 min.) with 3,4,5-trimethoxybenz-aldehyde (3.1 g ) to provide the cis silyl ether (2.2 g, oil ) and trans-isomer (2.98 g) as rods from ethanol, m.p. 128°-30° following chromatographic (silica gel, 9:1 hexane-ethyl acetate) separation of the Z/E mixture (1.2 g, 93% overall yield) of isomers. Cleavage (tetrabutylammonium fluoride, 20 min., tetrahydrofuran) of the silyl ether derivative of the Cis isomer (1.7 g) followed by column chromatographic (silica gel, 3:2 hexane-ethyl acetate) purification yielded combretastatin A-4 (1.15 g, 93%): fine crystals from ethyl acetate-hexane; mp 84.5-85.5 ; i.r. (NaCl) max 3395, 1580, 1508, 1462, 1456 1420, 1274, 1237, 1221, 1127, and 773 cm$^{-1}$.

Combretastatin A-4 and its trans-isomer were all found to be significantly active against the U.S. National Cancer Institute's (NCI) murine L1210 and P388 lymphocytic leukemia cell lines. Most importantly, combretastatin A-4 was found to compete with combretastatin A-1 as the most potent inhibitor of colchicine binding to tubulin yet discovered, to be a stalwart inhibitor of tubulin polymerization, to retard strongly ($ED_{50}$<0.003 μg/ml ) the growth of the murine lymphocytic leukemia L1210 and P388 cell lines as well as the VoLo, DLD-1 and HCT-15 human colon cancer ($ED50$ <0.01 μg/ml) cell lines, and to be the strongest antimitotic agent found among the *Combretum caffrum* constituents.

Biological evaluation (including in vivo ) of combretastatin A-4 is reported below.

The administration of combretastatin A-4 and its pharmacologically active physiologically compatible derivatives is useful for treating animals or humans having a neoplastic disease, for example, acute lymphocytic leukemia and the like using the accepted protocols of the National Cancer Institute.

The dosage administered will be dependent upon the identity of the neoplastic disease; the type of host involved, including its ages, health and weight; the kind of concurrent treatment, if any; and the frequency of treatment and therapeutic ratio.

Illustratively, dosage levels of the administered active ingredients are: intravenous, 0.1 to about 200 mg/kg; intramuscular, 1 to about 500 mg/kg; orally, 5 to about 1000 mg/kg; intranasal instillation, 5 to about 1000 mg/kg; and aerosol, 5 to about 1000 mg/kg of host body weight.

Expressed in terms of concentration, an active ingredient can be present in the compositions of the present invention for localized use about the cutis, intranasally, pharyngolaryngeally, bronichially, broncholially, intravaginally, rectally, or ocularly in a concentration of from about 0.01 to about 50% w/w of the composition; preferably about 1 to about 20% w/w of the composition; and for parenteral use in a concentration of from about 0.05 to about 50% w/v of the composition and preferably from about 5 to about 20% w/v.

The compositions of the present invention are preferably presented for administration to humans and animals in unit dosage forms, such as tablets, capsules, pills, powders, granules, suppositories, sterile parenteral solutions or suspensions, sterile non-parenteral solutions or suspensions, and oral solutions or suspensions and the like, containing suitable quantities of an active ingredient.

For oral administration either solid or fluid unit dosage forms can be prepared.

Powders are prepared quite simply by comminuting the active ingredient to a suitably fine size and mixing with a similarly comminuted diluent. The diluent can be an edible carbohydrate material as lactose or starch. Advantageously, a sweetening agent or sugar is present as well as a flavoring oil.

Capsules are produced by preparing a powder mixture as hereinbefore described and filling into formed gelatin sheaths. Advantageously, as an adjuvant to the filling operation, a lubricant such as a talc, magnesium sterate, calicum stearate and the like is added to the powder mixture before the filling operation.

Soft gelatin capsules are prepared by machine encapsulation of a slurry of active ingredients with an acceptable vegetable oil, light petrolatum or other inert oil or triglyceride.

Tablets are made by preparing a powder mixture, granulating or slugging, adding a lubricant and pressing into tablets. The powder mixture is prepared by mixing an active ingredient, suitably comminuted, with a diluent or base such as starch, lactose, kaolin, dicalcium phosphate and the like. The powder mixture can be granulated by wetting with a binder such as corn syrup, gelatin solution, methycellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

Advantageously the tablet can be provided with a protective coating consisting of a sealing coat or enteric coat of shellac, a coating of sugar and methylcellulose and polish coating of carnauba wax.

Fluid unit dosage forms for oral administration such as syrups, elixirs and suspensions can be prepared wherein each teaspoonful of composition contain a predetermined amount of active ingredient for administration. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit doages forms are prepared utilizing an active ingredient and a sterile vehicle, water being preferred. The active ingredient, depending on the form and concentration used, can be either suspended or dissolved in the vehicle. In preparing solutions the water-soluble active ingredient can be dissolved in water for injection and filter sterilized before filling into a suitable vial or ampule and sealing. Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and sterilization cannot be accomplished by filtration. The active ingredient can be sterilized by exposure to ethylene oxide before suspending in the sterile vehicle. Advantageously, a surfactant or wetting agent is included in the composition to facilitate uniform distribution of the active ingredient.

In addition to oral and parenteral administration, the rectal and vaginal routes can be utilized. An active ingredient can be administered by means of a suppository. A vehicle which has a melting point at about body temperature or one that is readily soluble can be utilized. For example, cocoa butter and various polyethylene glycols (Carbowaxes) can serve as the vehicle.

For intranasal instillation, a fluid unit dosage form is prepared utilizing an active ingredient and a suitable pharmaceutical vehicle, preferably P.F. water, a dry powder can be formulated when insufflation is the adminstration of choice.

For use as aerosols, the active ingredients can be packaged in a pressurized aerosol container together with a gaseous or liquefied propellant, for example, dichlorodifluromethane, carbon dioxide, nitrogen, propane, and the like, with the usual adjuvants such as cosolvents and wetting agents, as may be necessary or desirable.

The term "unit dosage form" as used in the specification and claims refers to physically discrete units suitable as unitary dosages for human and animal subjects, each unit containing a predetermined quantity of active material calculated to produce the desired thereapeutic effect in assocaition with the required pharamaceutical diluent, carrier or vehicle. The specifications for the novel unit dosage forms of this invention are dictated by and are directly dependent on (a) the unique characterisitcs of the active material and the particular therapeutic effect to be achieved, and (b) the limitation inherent in the art of compounding such active material for therapeutic use in humans, as disclosed in this specification, these being features of the present invention. Examples of suitable unit dosage forms in accord with this invention are tablets, capsules, troches, suppositories, powder packets, wafers, cachets, teaspoonfuls, tablespoonfuls, dropperfuls, ampules, vials, segregated multiples of any of the foregoing, and other forms as herein described.

The combretastatin active ingredients to be employed as antineoplastic agents can be easily prepared in such unit dosage form with the employment of pharamaceutical materials which themselves are available in the art and can be prepared by established procedures. Illustrative of the preparation of the unit dosage forms, and not as a limitation thereof, are set forth in Example 6 supra.

To further assist in the understanding of the present invention the following examples are presented to more clearly disclose the present invention and not by way of limitation.

EXAMPLE 1

Plant Taxonomy

Stem of the South African tree *Combretum caffrum* (Eckl. and Zeyh) Kuntze was collected and identified as part of the National Cancer Institute-U.S. Department of Agriculture research program directed by Drs. John D. Douros, Matthew I. Suffness and James A. Duke. The stem wood (B817373) employed in this study was obtained in 1979.

EXAMLE 2

Extraction and Solvent Partition Procedures

The dry stem wood (77 kg) of *Combretum caffrum* was subdivided by chipping and extracted with 1:1 methylene chloride-methanol (320 liters) at ambient temperature for eleven days. The methylene chloride phase was separated by addition of water (25% by volume) and the plant extraction was repeated with another 320 liters of methylene chloride-methanol 1:1 as just described. The combined methylene chloride phases were concentrated to a crude extract weighing 1.42 kg and showing PS in vivo life extension of 27% at 100 mg/kg and PS $ED_{50}$ 5.1 μg/ml. A solution of the methylene chloride fraction was partitioned 5× between hexane (18 liters) and methonal-water (9:1, 18 liters). After separating the hexane phase the methonal-water was adjusted to a concentration of 3:2 and extracted (5×) with methylene chloride (18 liters). The hexane extract (602.3 g) provded PS in vivo inactive and marginally active against the cell line with $ED_{50}$ 2.4 μg/ml. The PS in vivo activity (38–41% life extension at 25–50 mg/kg) and major cell growth inhibition ($ED_{50}$ 0.21 μg/mL) was concentrated in the methylene chloride fraction (827.9 g) from the solvent partitioning sequence.

EXAMPLE 3

Isolation of Combretastatin A-4

The methylene chloride fraction from the solvent partitioning sequence was dissolved in methanol (7×500 mL) and further separated by steric exclusion chromatography on columns of Sephadex LH-20 (7×2.5 kg). The PS active (41% life extension at 12.5 mg/kg and $ED_{50}$ 0.18 mg/mL fraction (30.6 g) was further separated in hexane-toluene-methanol (3:1:1) solution by partition chromatography on Sephadex LH-20 (2.5 kg). Continued elution with hexane-toluene-methonal (3:1:1) furnished a fraction (2.4g) showing activity ($ED_{50}$ 0.1 g/ml) in PS system containing the compounds of lesser polarity and thus eluted prior to the combretastatin A-3 and B-2. Silica gel chromatography of a part (2.2g) of the fraction and elution with hexane-ethyl acetate (3:1) afforded 4′-hydroxy-3,5-dimehoxybibenzyl, 2-hydroxy-3,4,6,7-tetramethoxy-9. 10-dihydrophananthrene, and yet another very active fraction (0.56g, $ED_{50}$ $4.0\times 10^{-}$'μg/ml). Now this latter fraction was rechromatographed in hexane-ethyl acetate (4:1) on a similar silica gel column and thus the PS activity was concentrated in two fractions. The relatively nonpolar and less active ($ED_{50}$ 0.26 g/ml) fraction upon HPLC on Partisil M-9 (10×500mm) column and elution with hexane-2-propanol (9:1) gave 4′-hydroxy-3,4,5-trimethoxy bibenzyl. Whereas the relatively polar and more active ($ED_{50}$ $3.4\times 10^{-2}$ μg/ml) fraction after several PLC and HPLC (Partisil M-9) in hexane-2-propanol (9:1) provided an apparently pure fraction. Analysis of $^{1}H$-NMR (400 $MH_z$) and $^{13}C$-NMR (100 $MH_z$) of this fraction revealed that it was a mixture of at least three similar compounds. It was very clear from the NMR spectral analysis that these compounds were stilbenic in nature. Therefore, a part (10mg) was hydrogenated with 5% Palladium on carbon (10mg) in Methanol (10ml) for 48 hours. Unfortunately, no chromatographic resolution was achieved on thus prepared two component ($^{1}H$-NMR) mixture of the dihydro derivatives. Finally, successful separation of the stilbenes was achieved after silyltion of a part of the olefinic mixture as described below.

To a solution of stilbenic mixture (7.1 mg) in DMF (2ml) was added diisopropylethyl amine (1ml) and stirred under argon for ten minutes. Tert-butyldimethylsilyl chloride (100 mg) was added and stirred for one hour. Ice (1g) and then saturated aqueous solution of sodium bicarbonate (5 ml) was added. This mixture was extracted with ether (2×10ml), washed once with saturated $NaHCO_3$ solution (10ml) and water (10ml), dried and evaporated to give an oily mixture of three major components on silica gel TLC, (hexane-ethyl acetate, 17:3) to give the tert-butyldimethyl silyl ether of combretastatin A-4 as least polar component (Rf 0.37) as an oil (3.0mg): IR max (NaCl) 2955, 2931, 1580, 1508, 1466, 1281, 1249, 1236, 1128, 841 cm$^-$, $^1$H-NMR (400 MHz) 0.059 (6H,s), 0.929 (9H,s), 3.702 (6H, s, 2×OCH$_3$), 3.832 (6H, s, 2×OCH$_3$), 6.429 (1H, d, J=12.16Hz), 6.463 (1H, d, J=12.16 Hz), 6.499(2H,s), 6.735(1H, d, J=8.28 Hz), 6.790 (1H, d, J=2.0 Hz), 6.852 (1H, dd, J=8.28, 2.0 Hz). HREIMS (m/z): 430.2168 (26%, M$^+$, calcd for C$_{24}$H$_{34}$O$_5$Si: 430.2175), 374.1511 (5%), 358.1238 (100).

EXAMPLE 4

3'-[(tert-Butyldimethylisilyl)oxy]-3,4,4',5-tetramethoxy (Z) and (E)- stilbene:
3'-[(tert-Butyldimenthylsilyl)oxy]-combretastatin A-4 and its trans isomer To a cooled (−20°) mixture of 3-[(tert-butyldimenthyl-silyl)oxy]-4-methoxy benzlphoshonium bromide (11.89 g, 20 mmol) in THF (300 ml) was added n-butyl lithium (13.3 ml, 20 mmol) under argon and red solution that thus appeared was stirred at room temperature for 20 minutes. 3,4,5-trimethoxy benzaldehyde (3.14 g, 16 mmol) was added to the mixture. Red color was discharged and reaction was complete in ten minutes. Ice water (100 ml) was added followed by ether (300 ml). The organic layer was washed with cold water (2×100 ml), dried (Na$_2$SO$_4$) and evaporated to give an oil. Flash chromatography on silica gel of the oil and elution with hexane-ethyl acetate (9:1) afforded the Z isomer (2.2 g) as oil. TLC, IR $^1$NMR, HREIMS was found to be identical with the combretastatin A-4 silyl ether. Anal: Calcd for C$_{24}$H$_{34}$O$_5$Si: C, 66.95; H, 7.96. Found: c, 67.39, H, 8.22.

Continued elution gave a mixture of Z/E isomers (1.23 g) and finally the E-isomer (2.98 g, total reaction yield 93.0%, ratio Z/E 1:1.5), Recrystallization of the E-isomer afforded rods, mp 128°-30°, IR max (NaCl) 2955, 2931, 2856, 1582, 1509, 1464, 1424, 1273, 1251, 1129 cm$^{-1}$, $^1$H-NMR (400MHz) 0.186 (6H,s), 1.025 (9H,s), 3.830 (3H, s), 3.864 (3H, s), 3.917 (6H, s, 2×OCH$_3$) 6.712 (2H,s), 6.833 (1H, d, J=8.12 Hz), 6.855 (1H, d, J=16.28 Hz), 6.896 (1H, d, J=16.28 Hz), 7.035(1H, d, J=2.0 Hz), 7.055 (1H, dd, J=8.12, 2.0 Hz). HREIMS (m/z): 430.2168 (22%, M$^+$, calcd for C$_{24}$H$_{34}$O$_5$Si: 430.2175), 373.1469 (20%), 358.1235 (79%). Anal. calcd for C$_{24}$H$_{34}$O$_5$Si: C, 66.95; H7.96. Found C, 67.16; H, 8.20.

EXAMPLE 5

Combretastatin A-4

The synthetic silyl ether (1.68 g, 3.9 mmol) in THF (40 ml) was allowed to react under argon with tetrabutylammonium fluoride (4.0 ml, 4.0 mmol) for 20 minutes. Ice (10 g) was added followed by ether (100 ml). The ethereal solution was washed with water (3×40 ml), dried, evaporated and filtered through a silica gel column in hexane-ethyl acetate (3:2) to give combretastatin A-4 (1.15 g, 92.7%) as a gum. Recrystallization from ethyl acetate-hexane gave fine granules, mp 84.5°-85.5°; IR max (NaCl) 3395, 1580, 1508, 1462, 1456, 1420, 1274, 1237, 1221, 1127, 773 cm$^{-1}$, $^1$H-NMR (400 MHz) 3.700 (3H, s); 3.844 (3H, s), 3.869 (3H, s), 5.509 (1H, brs), 6.412 (1H, d, J=12.16 Hz), 6.471 (1H, d, J=12.16 Hz), 6.527 (2H, s), 6.734 (1H, d, J=8.4 Hz), 6.799 (1H, dd, J=8.4, 2.04 Hz), 6.925 (1H, d, J=2.04 Hz), $^{13}$C-NMR (100.63 MHz), 55.89 (3 C), 60.85, 106.07 (2 C), 110.32, 115.02, 121.06, 128.98, 129.45, 130.58, 132.67, 137.14, 145.22, 145.77, 152.82 (2 c).

Anal. calcd for C$_{18}$H$_{20}$O$_5$: C, 68.35; H, 6.37. Found C, 68.53; H, 6.47.

EXAMPLE 6

Dosage Forms

Several dosage forms were prepared embodying the present invention. They are shown in the following examples in which the notation "active ingredient" signifies combretastatin A-4, its synthetic counterparts and the non-toxic pharmaceutically active derivatives thereof.

COMPOSITION "A"

Hard-Gelatin Capsules

One thousand two-piece hard gelation capsules for oral use, each capsule containing 200 mg of an active ingredient are prepared from the following types and amounts of ingredients:

| | |
|---|---|
| Active ingredient, micronized | 200 gm |
| Corn Starch | 20 gm |
| Talc | 20 gm |
| Magnesium stearate | 2 gm |

The active ingredient, finely divided by means of an air micronizer, is added to the other finely powdered ingredients, mixed thoroughly and then encapsulated in the usual manner.

The foregoing capsules are useful for treating a neoplastic disease by the oral administration of one or two capsules one to four times a day.

Using the procedure above, capsules are similarly prepared containing a active ingredient in 50, 250 and 500 mg amounts by substituting 50 gm, 250 gm and 500 gm of a active ingredient for the 200 gm used above.

COMPOSITION "B"

Soft Gelatin Capsules

One-piece soft gelatin capsules for oral use, each containing 200 mg of a active ingredient (finely divided by means of an air micronizer), are prepared by first suspending the compound in 0.5 ml of corn oil to render the material capsulatable and then capsulating in the above manner.

The foregoing capsules are useful for treating a neoplastic disease by the oral administration of one or two capsules one to four times a day.

COMPOSITION "C"

Tablets

One thousand tablets, each containing 200 mg of a active ingredient are prepared from the following types and amounts of ingredients:

| | |
|---|---|
| Active ingredient micronized | 200 gm |
| Lactose | 300 gm |
| Corn starch | 50 gm |
| Magnesium stearate | 4 gm |
| Light liquid petrolatum | 5 gm |

The active ingredient finely divided by means of an air micronizer, is added to the other ingredients and then mixed thoroughly and slugged. The slugs are broken down by forcing through a Number Sixteen screen. The resulting granules are then compressed into tablets, each tablet containing 200 mg of the active ingredient.

The foregoing tablets are useful for treating a neoplastic disease by the oral administration of one or two tablets one to four times a day.

Using the procedure above, tablets are similarly prepared containing a active ingredient in 250 mg and 100 mg amounts by substituting 250 gm and 100 gm of a active ingredient for the 200 gm used above.

COMPOSITION "D"

Oral Suspension

One thousand ml of an aqueous suspension for oral use, containing in each teaspoonful (5 ml) dose, 50 mg of a active ingredient, is prepared from the following types and amounts of ingredients:

| Active ingredient micronized | 10 gm |
|---|---|
| Citric acid | 2 gm |
| Benzoic acid | 1 gm |
| Sucrose | 790 gm |
| Tragacanth | 5 gm |
| Lemon Oil | 2 gm |
| Deionized water, q.s. 1000 ml. | |

The citric acid, benzoic acid, sucrose, tragacanth and lemon oil are dispersed in sufficient water to make 850 ml of suspension. The active ingredient finely divided by means of an air micronizer, is stirred into the syrup until uniformly distributed. Sufficient water is added to make 1000 ml.

The composition so prepared is useful for treating a neoplastic disease at a dose of 1 tablespoonful (15 ml) three times a day.

COMPOSITION "E"

Parenteral Product

A sterile aqueous suspension for parenteral injection, containing in 1 ml 300 mg of a active ingredient for treating a neoplastic disease, is prepared from the following types and amounts of ingredients:

| Active ingredient, micronized | 30 gm |
|---|---|
| Polysorbate 80 | 5 gm |
| Methylparaben | 2.5 gm |
| Propylparaben | 0.17 gm |
| Water for injection, q.s. 1000 ml. | |

All the ingredients, except the active ingredient, are dissolved in the water and the solution sterilized by filtration. To the sterile solution is added the sterilized active ingredient, finely divided by means of an air micronizer, and the final suspension is filled into sterile vials and the vials sealed.

The composition so prepared is useful for treating a neoplastic disease at a dose of 1 milliliter (1M) three times a day.

COMPOSITION "F"

Suppository, Rectal and Vaginal

One thousand suppositories, each weighing 2.5 gm and containing 200 mg of a active ingredient are prepared from the following types and amounts of ingredients:

| Active ingredient, micronized | 15 gm |
|---|---|
| Propylene glycol | 150 gm |
| Polyethylene glycol #4000, q.s. | 2,500 gm |

The active ingredient is finely divided by means of an air micronizer and added to the propylene glycol and the mixture passed through a colloid mill until uniformly dispersed. The polyethylene glycol is melted and the propylene glycol dispersion added slowly with stirring. The suspension is poured into unchilled molds at 40° C. The composition is allowed to cool and solidify and then removed from the mold and each suppository foil wrapped.

The foregoing suppositories are inserted rectally or vaginally for treating a neoplastic disease.

COMPOSITION "G"

Intranasal Suspension

One thousand ml of a sterile aqueous suspension for intranasal instillation, containing in each ml 200 mg of a active ingredient, is prepared from the following types and amounts of ingredients:

| Active ingredient, micronized | 15 gm |
|---|---|
| Polysorbate 80 | 5 gm |
| Methylparaben | 2.5 gm |
| Propylparaben | 0.17 gm |
| Deionized water, q.s. 1000 ml. | |

All the ingredients, except the active ingredient, are dissolved in the water and the solution sterilized by filtration. To the sterile solution is added the sterilized active ingredient, finely divided by means of an air micronizer, and the final suspension is aseptically filed into sterile containers.

The composition so prepared is useful for treating a neoplastic disease, by intranasal instillation of 0.2 to 0.5 ml given one to four times per day.

An active ingredient can also be present, as shown in Compositions H, I, and J in the undiluted pure form for use locally about the cutis, intranasally, pharyngolaryngeally, bronchially, broncholially or orally.

COMPOSITION "H"

Powder

Five grams of a active ingredient in bulk form is finely divided by means of an air micronizer. The micronized powder is placed in a shaker-type container.

The foregoing composition is useful for treating a neoplastic disease, at localized sites by applying a powder one to four times per day.

COMPOSITION "I"

Oral Powder

One hundred grams of a active ingredient in bulk form is finely divided by means of an air micronizer. The micronized powder is divided into individual doses of 200 mg and packaged.

The foregoing powders are useful for treating a neoplastic disease, by the oral administration of one or two powders suspended in a glass of water, one to four times per day.

COMPOSITION "J"

Insufflation

One hundred grams of a active ingredient in bulk form is finely divided by means of an air micronizer.

The foregoing composition is useful for treating a neoplastic disease, by the inhalation of 300 mg one to four times per day.

COMPOSITION "K"

Hard Gelatin Capsules

One hundred two-piece hard gelatin capsules for oral use, each capsule containing 200 mg of a active ingredient.

The active ingredient is finely divided by means of an air micronizer and encapsulated in the usual manner.

The foregoing capsules are useful for treating a neoplastic disease, by the oral administration of one or two capsules, one to four times a day.

Using the procedure above, capsules are similarly prepared containing active ingredient in 50, 250 and 500 mg amounts by substituting 50 gm, 250 gm and 500 gm of the active ingredient for the 200 gm used above.

From the foregoing, it is apparent that an invention has been herein described and illustrated which fulfills all of the aforestated objectives in a remarkably unexpected fashion. It is of course understood that such modifications, alterations and adaptations as may readily occur to the artisan confronted with this disclosure are intended within the spirit of this disclosure which is limited only by the scope of the claims appended hereto.

Accordingly, what is claimed is:

1. A compound denominated combretastatin A-4 and for inhibiting tubulin polymerization having the structural formula:

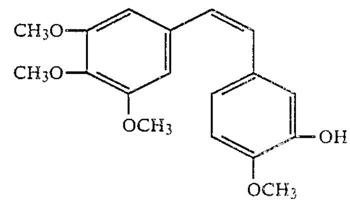

2. A pharmaceutical preparation containing a pharmacologically acceptable carrier and, as its essential active ingredient, a compound denominated combretastatin A-4 having the structural formula:

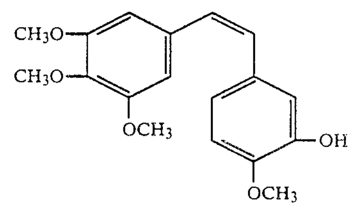

3. A method of treating a host afflicted with a neoplastic disease selected from the group consisting of lymphocytic leukemia and human colon cancer comprising administering to said host a cell-growth inhibitory amount of a natural or synthetic substance denominated combretastatin A-4 or a pharmaceutically active non-toxic derivative thereof in a pharmaceutically acceptable carrier, said substance having the structural formula:

* * * * *